T863002

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED JUNE 24, 1969

863 O.G. 999

726,610

PROCESS FOR PREPARING UNSATURATED ALIPHATIC ALDEHYDES AND MONOCARBOXYLIC ACIDS

Howard S. Young and Edgar L. McDaniel, Kingsport, Tenn., assignors to Eastman Kodak Company, Rochester, N.Y., a corporation of New Jersey

Continuation of application Ser. No. 375,286, June 15, 1964. This application May 3, 1968. Published June 24, 1969

Int. Cl. C07c *27/12, 51/20;* B01j *11/32*

U.S. Cl. 260—604

No Drawing. 21 Pages Specification

Acrolein and acrylic acid or methacrolein and methacrylic acid are manufactured by contacting vaporized propylene or isobutylene with oxygen at an elevated temperature, e.g., about 300° C. to about 600° C., in the presence of a supported catalyst essentially consisting of a calcined mixture of (1) an oxide of arsenic and (2) a heteropoly acid or molybdenum containing cerium as the central atom, e.g., cerimolybdic acid. The catalyst can also contain an oxide of chromium, iron, or boron or mixtures thereof. Preferably the catalyst contains 1% to 20% by weight of the oxide of arsenic and 5% to 60% of the heteropoly acid.